(12) United States Patent
Barclay

(10) Patent No.: US 7,195,791 B2
(45) Date of Patent: *Mar. 27, 2007

(54) METHOD FOR PRODUCTION OF ARCHIDONIC ACID

(75) Inventor: William R. Barclay, Boulder, CO (US)

(73) Assignee: Martek Biosciences Corporation, Columbia, MD (US)

(*) Notice: Subject to any disclaimer, the term of this patent is extended or adjusted under 35 U.S.C. 154(b) by 289 days.

This patent is subject to a terminal disclaimer.

(21) Appl. No.: 10/802,392

(22) Filed: Mar. 4, 2004

(65) Prior Publication Data

US 2004/0248266 A1 Dec. 9, 2004

Related U.S. Application Data

(60) Continuation of application No. 09/972,550, filed on Oct. 5, 2001, now Pat. No. 6,749,849, which is a division of application No. 09/480,060, filed on Jan. 10, 2000, now Pat. No. 6,319,698, which is a continuation of application No. 09/270,294, filed on Mar. 15, 1999, now Pat. No. 6,245,365, which is a continuation of application No. 08/763,973, filed on Dec. 10, 1996, now Pat. No. 5,882,703, which is a division of application No. 08/377,766, filed on Jan. 24, 1995, now Pat. No. 5,583,019.

(51) Int. Cl.
*A23C 9/12* (2006.01)
*A23J 1/18* (2006.01)
*C12P 7/64* (2006.01)
*A23L 1/28* (2006.01)

(52) U.S. Cl. ............ 426/61; 435/93.5; 426/7; 426/42; 426/43; 426/60; 426/491; 426/492; 426/580; 426/581; 426/588; 426/601

(58) Field of Classification Search .......... 426/7, 426/42, 43, 60, 61, 491, 492, 580, 581, 588, 426/661; 435/134; 424/93.5
See application file for complete search history.

(56) References Cited

U.S. PATENT DOCUMENTS

| 4,783,408 | A | 11/1988 | Suzuki et al. ........ 435/134 |
|---|---|---|---|
| 5,204,250 | A | 4/1993 | Shinmen et al. ..... 435/134 |
| 5,374,657 | A | 12/1994 | Kyle .................... 514/547 |
| 5,518,751 | A | 5/1996 | De Boer et al. ..... 426/585 |
| 5,550,156 | A | 8/1996 | Kyle .................... 514/547 |
| 5,583,019 | A | 12/1996 | Barclay .............. 435/134 |
| 5,658,767 | A | 8/1997 | Kyle .................... 435/134 |
| 5,882,703 | A | 3/1999 | Barclay .............. 426/7 |
| 6,245,365 | B1 | 6/2001 | Barclay .............. 426/7 |
| 6,319,698 | B1* | 11/2001 | Barclay .............. 435/134 |
| 6,541,049 | B2* | 4/2003 | Barclay .............. 426/7 |
| 6,749,849 | B2* | 6/2004 | Barclay .............. 424/93.5 |

FOREIGN PATENT DOCUMENTS

| EP | 0 276541 A | 8/1988 |
|---|---|---|
| JP | A-S63-12290 | 1/1988 |
| JP | A-S63-68090 | 3/1988 |
| JP | 01304892 | 12/1989 |
| JP | A H03-272692 | 12/1991 |
| JP | 163142 | 6/1993 |
| WO | 3920679 A1 | 12/1990 |
| WO | WO 91/07498 | 5/1991 |
| WO | WO 92/13086 | 8/1992 |
| WO | WO 96/21037 | 7/1996 |
| WO | WO 94/28913 | 12/1997 |

OTHER PUBLICATIONS

Bajpai et al. pp. 1-10, 1992, *Biotechnol. Appl. Biochem.*, vol. 15.
Bajpai et al., pp. 1255-1258, 1991, *App. Environ. Microbiol.*, vol. 57, No. 4.
Bajpai et al., pp. 775-780, 1991, *JAOCS*, vol. 68, No. 10.
Computer Abstract JP63296665 Seven Tech KK Pub Dec. 1988.
Computer Abstract Yoshio JP06271464 Pub Sep. 1994.
Gandhi et al., pp. 1825-1830, 1991, *J. Gen. Microbiol.*, vol. 137.
Kendrick et al., pp. 15-20, 1992, *Lipids*, vol. 27, No. 1.
Radwan, pp. 421-430, 1991, *Appl. Microbiol. Biotechnol.*, vol. 35.
Sajbidor et al., pp. 455-456, 1990, *Biotechnol. Letters*, vol. 12, No. 6.
Shinmen et al., pp. 11-16, 1989, *Appl. Microbiol. Biotechnol.*, vol. 31.
Shimizu et al., pp. 509-512, *Lipids*, vol. 27, No. 7 (1992).
Shimizu et al., pp. 254-258, 1991, *JAOCS*, vol. 68, No. 4.
Shimizu et al., pp. 342-347, 1989, *JAOCS*, vol. 66, No. 3.
Shimizu et al., pp. 1455-1459, 1988, *JAOCS*, vol. 65, No. 9.
Totani et al. pp. 52-60, in *Industrial Applications of Single Cell Oils* (Kyle, J. ed.), 1992, American Oil Chemists' Society, Champaign, ILL.
Totani et al., pp. 1060-1062, 1987, *Lipids*, vol. 22, No. 12.
APS ABS. J57-86254, Fujita et al., May 29, 1982.
APS ABS J06-271464. Shimizu Sep. 27, 1994.
APS ABS J07-59540 Shimizu Mar. 7, 1995.
Yamada et al., *J. Disp. Sc. Techn.*, 10(4&5):561-579 (1989).
Translation of Yamada et al., a company publication of Daiichi Kogyo Yakuhin, which publication was received by the Japanese National Diet Library on Jul. 12, 1990 and availiable to the public shortly after said date.
Computer Dechema Abstract CEABA: 1993:1518691 Kyle "Arachidonic acid and Methods for the production and Use Thereof" 1993.

(Continued)

*Primary Examiner*—Herbert J. Lilling
(74) *Attorney, Agent, or Firm*—Sheridan Ross P.C.

(57) ABSTRACT

The present invention relates to a process for producing arachidonic acid. In one embodiment, *Mortierella* sect. *schmuckeri* microorganisms are cultured in fermentation medium, preferably containing a component of a complex nitrogen source. Further disclosed is a food product which includes *Mortierella* sect. *schmuckeri* microorganisms or lipid isolated from such microorganisms to enhance the arachidonic acid content of the food product.

10 Claims, No Drawings

OTHER PUBLICATIONS

Computer WPIDS Abstract JP63296665 Mar. 1993.
Computer Biosis Abstract 1994:531085 Chang, et al. "Production of Arachidonic Acid by Mortierlla AlpIna" J. Chinese Agr. Chem. Soc. 1994 32:395-05.

Computer Biosis Abstract 1993:522102 Stred'anska et al. "Arachidonic Acid Production by Mortierella alpina" World Journal Microbiol & Biotech 1993 9:511-13.

* cited by examiner

METHOD FOR PRODUCTION OF ARACHIDONIC ACID

CROSS-REFERENCE TO RELATED APPLICATIONS

This application is a continuation of U.S. patent application Ser. No. 09/972,550, filed Oct. 5, 2001 now U.S. Pat. No. 6,749,849, which is a divisional of U.S. patent application Ser. No. 09/480,060, filed Jan. 10, 2000, now U.S. Pat. No. 6,319,698, which is a continuation of U.S. patent application Ser. No. 09/270,294, filed Mar. 15, 1999, now U.S. Pat. No. 6,245,365, which is a continuation of U.S. patent application Ser. No. 08/763,973, filed Dec. 10, 1996, now U.S. Pat. No. 5,882,703, which is a divisional of U.S. patent application Ser. No. 08/377,766, filed Jan. 24, 1995, now U.S. Pat. No. 5,583,019. The entire disclosure of U.S. patent application Ser. No. 09/972,550 is incorporated herein by reference.

FIELD OF THE INVENTION

The present invention relates to a process for production of arachidonic acid. The present invention also relates to a food product and a method to make the food product containing such arachidonic acid.

BACKGROUND OF THE INVENTION

Arachidonic acid (all-cis-5,8,11,14-eicosatetraenoic acid) is a polyunsaturated fatty acid (PUFA) containing 20 carbon atoms with four double bonds. The double bonds are arranged with the last one located six carbon atoms from the methyl end of the chain. Therefore, arachidonic acid is referred to as an omega-6 fatty acid. Arachidonic acid is one of the most abundant $C_{20}$ PUFA's in the human body. It is particularly prevalent in organ, muscle and blood tissues. Arachidonic acid is a direct precursor for a number of circulating eicosenoids, such as prostaglandins, thromboxanes, leukotrienes and prostacyclins, which are important biological regulators. These eicosenoids exhibit regulatory effects on lipoprotein metabolism, blood rheology, vascular tone, leukocyte function, platelet activation and cell growth. The application of arachidonic acid to an infant's diet is particularly important due to the rapid body growth of an infant. Arachidonic acid is an important precursor to many of the eicosanoids which regulate cellular metabolism and growth in infants. It is found naturally in human breast milk but not in most infant formula. In an effort to have infant formula match the long chain fatty acid profile found in breast milk, scientific and food regulatory bodies have recommended that arachidonic acid be added to infant formula, especially in formula utilized for premature infants.

In particular, it is preferable that arachidonic acid containing oil produced for use with infant formula contain little or no other long chain highly unsaturated fatty acids (e.g., eicosapentanoic acid). Such other long chain highly unsaturated fatty acids are not preferred because some of these fatty acids can interfere with the utilization of arachidonic acid by the infant, and/or can inhibit blending of the arachidonic acid-containing oil with other oils to achieve the appropriate ratio of fatty acids matching breast milk or other desired applications. Highly unsaturated fatty acids are defined as fatty acids containing 4 or more double bonds.

Traditional sources of arachidonic acid include poultry eggs, bovine brain tissue, pig adrenal gland, pig liver and sardines. The yield of arachidonic acid, however, is usually less than 0.2% on a dry weight basis. The use of microorganisms capable of producing arachidonic acid de novo have been suggested by various investigators, including Kyle, PCT Publication No. WO 92/13086, published Aug. 6, 1992; Shinmen et al., U.S. Pat. No. 5,204,250, issued Apr. 20, 1993; Shinmen et al., pp. 11–16, 1989, *Appl. Microbiol. Biotechnol.*, vol. 31; Totani et al., pp. 1060–1062, 1987, *LIPIDS, vol.* 22; Shimizu et al., pp. 509–512, 1992, *LIPIDS*, vol. 27; Shimizu et al., pp. 342–347, 1989, *JAOCS*, vol. 66; Shimizu et al., pp. 1455–1459, 1988, *JAOCS*, vol. 65; Shimizu et al., pp. 254–258, 1991, *JAOCS*, vol. 68; Sajbidor et al., pp. 455–456, 1990, *Biotechnology Letters*, vol. 12; Bajpai et al., pp. 1255–1258, 1991, *Appl. Environ. Microbiol.*, vol. 57; Bajpai, pp. 775–780, 1991, *JAOCS*, vol. 68; and Gandhi et al., pp. 1825–1830, 1991, *J. Gen. Microbiol.*, vol. 137. The arachidonic acid productivity by the microorganisms disclosed by prior investigators, however, is less than 0.67 grams per liter per day. Such amounts are significantly less than the amounts of arachidonic acid produced by the microorganisms of the present invention. These lower productivity values are the result of employing strains: (1) with slow growth or lipid production rates leading to long fermentation times (i.e., greater than 2–3 days) (Kyle, 1992, *ibid.*; Shinmen et al., 1993, *ibid.*; Shinmen et al., 1989, *ibid.*; Bajpai et al., 1991, *ibid.*; Bajpai, *ibid.*; and Gandhi et al., *ibid.*); and/or (2) that contain low arachidonic acid contents (expressed as % fatty acids) in the final oil produced (Shinmen et al., 1993, *ibid.*; Shimizu et al., 1989, *ibid.*; and Kendrick and Ratledge, 1992, pp. 15–20, *Lipids*, vol. 27); and/or (3) which require long periods of stress (i.e., aging a biomass for 6–28 days) to achieve high levels of arachidonic acid in a biomass (Bajpai et al., 1991, *ibid.* and Shinmen et al., 1989, *ibid.*); and/or (4) that only exhibit high arachidonic acid content in non-commercial growth conditions (e.g., malt agar plates) (Totani and Oba, 1987, pp. 1060–1062, *Lipids*, vol. 22). In addition, non-*Mortierella schmuckeri* microorganisms that have been proposed for producing arachidonic acid, in particular *Pythium insidiosum* microorganisms, disclosed by prior investigators (Kyle, 1992, *ibid.*), have been reported to be pathogenic to humans and/or animals.

Thus, there remains a need for an economical, commercially feasible method for producing arachidonic acid. The present invention satisfies that need. There also remains a need for the an economical, commercially feasible food product for the introduction of arachidonic acid produced according to the present invention into the diet of human infants.

SUMMARY

The present invention provides for a method for economically producing arachidonic acid. One embodiment of the present invention includes a method to produce arachidonic acid, comprising culturing microorganisms of the genus *Mortierella* sect. *schmuckeri* in a medium comprising a source of assimilable organic carbon and a source of assimilable nitrogen. In another embodiment, such strains of *Mortierella* sect. *schmuckeri* are capable of producing at least about 0.86 grams per liter per day of arachidonic acid.

Yet another embodiment of the present invention includes a food product comprising lipids recovered from a microorganism of the genus *Mortierella* sect *schmuckeri* and a food material. In particular, such lipids can be added to infant formula and baby food to increase the arachidonic acid or long chain omega-6 fatty acid content of such foods.

DETAILED DESCRIPTION OF THE INVENTION

The present invention provides for a novel process for the production of commercially feasible amounts of arachidonic acid using a *Mortierella* sect. *schmuckeri* microorganism. One embodiment of the present process is to produce arachidonic acid by culturing microorganisms of the genus *Mortierella* sect. *schmuckeri* in a medium comprising a source of assimilable organic carbon and a source of assimilable nitrogen. The lower fungi Phycomycetes contains at least two classes, including Oomycetes and Zygomycetes. The class Zygomycetes contains at least two orders, including Entomophthorales and Mucorales. Contained within the Mucorales order are numerous genera including *Mortierella*. The genus *Mortierella* contains nine sections, including sect. *schmuckeri* (Gams, 1977, pp. 381–391, *Persoonia*, vol. 9 and Gams, 1977, p. 216, in Abstracts Vol. A–L, Second International Mycological Congress, University of South Florida). The *schmuckeri* sect. of the genus *Mortierella* contains three species referred to as *Mortierella camargensis, Mortierella clausenii* and *Mortierella schmuckeri*.

All of the other strains of *Mortierella* that have been evaluated for arachidonic acid production belong to the *Mortierella* sections *alpina, hygrophila* or *spinosa*. It has now been recognized that strains of *Mortierella* sect. *schmuckeri* are particularly advantageous in the production of arachidonic acid compared to these other strains of *Mortierella*. In particular, it has been found that strains of *Mortierella* sect. *schmuckeri* are capable of producing arachidonic acid with high productivity. Strains of *Mortierella* sect. *schmuckeri* of the present invention are preferably capable of producing at least about 0.70 grams of arachidonic acid per liter per day, more preferably at least about 0.80 grams of arachidonic acid per liter per day, and even more preferably at least about 0.86 grams of arachidonic acid per liter per day. Preferably, strains of *Mortierella* sect. *schmuckeri* of the present invention are also capable of producing a total fatty acid content of at least about 20% of dry weight, preferably at least about 30% of dry weight, and more preferably at least about 40% of dry weight. Moreover, preferred strains of *Mortierella* sect. *schmuckeri* of the present invention contain at least about 20% of total fatty acids as arachidonic acid, more preferably at least about 35% total fatty acids as arachidonic acid, and even more preferably at least about 48% total fatty acids as arachidonic acid. The arachidonic acid content of cellular biomass of strains of *Mortierella* sect. *schmuckeri* of the present invention can be at least about 5% of cellular dry weight, preferably at least about 8% of cellular dry weight, and more preferably at least about 13% of cellular dry weight.

Oil recovered, such as by extraction, from a preferred strain of *Mortierella* sect. *schmuckeri* of the present invention contains at least about 20% arachidonic acid, more preferably at least about 30% arachidonic acid, and even more preferably at least about 41% arachidonic acid. As used herein, "lipid" "lipid extract", "oil" and "oil extract" are used interchangeably.

Morphological growth forms of fungi can have a significant effect on growth and product formation in fermenters. Fungal morphology in fermenters can range from a dispersed filamentous form to a dense pellet form. Species of *Mortierella* sect. *schmuckeri* of the present invention have an advantage over previously utilized species of *Mortierella*, including the ability to readily grow (early in a fermentation) in a dispersed filamentous form when grown in agitated liquid cultures such as shake flasks or fermenters. Some other species of *Mortierella* grown in fermentation medium typically grow in the form of pellets or spherical aggregates (i.e., having the appearance of a very tight cotton ball), sometimes exhibiting a dispersed form only after several days in a fermentation. Without being bound by theory, it is believed that the growth and productivity of cells in the pellet form is limited because cells in the center of a pellet or aggregate are not exposed to the necessary nutrients contained in the fermentation medium. Traditional methods of growing these fungal populations can include increasing the agitation of the fermenter or addition of detergents in an attempt to disperse such aggregates and improve cell growth. The present inventor has discovered that strains of *Mortierella* sect. *schmuckeri* of the present invention readily grow in the dispersed filamentous form, thereby improving growth and productivity of such cells by enabling nutrients to reach all the cells. As used herein, the term "filamentous" refers to the growth of fungi as a loosely branched network of short mycelia rather than as a pellet or aggregate.

Preferred strains of *Mortierella* sect. *schmuckeri* of the present invention include strains of *Mortierella* sect. *schmuckeri* isolated from cold, arid soil, in which the microorganisms experience short periods of wetness. In particular, such areas can include soils that experience some prolonged periods of freezing or near freezing conditions. More preferred strains of *Mortierella* sect. *schmuckeri* are isolated from the Southwest region of North America, in particular, desert regions of the United States and/or Mexico. In particular, strains of *Mortierella* sect. *schmuckeri* of the species *Mortierella schmuckeri* are isolated from southern California and/or Mexico.

Strains of *Mortierella* can be isolated from soils or aquatic habitats using techniques known in the art (Stevens, 1974, in *Mycology Guidebook*, University of Washington Press, Seattle; and Barron, pp. 405–427, 1971, in *Methods of Microbiology*, Vol. 4.). More specifically, species of *Mortierella* sect. *schmuckeri* can be isolated by suspending small samples of soil in distilled water and then streaking a portion of the suspension on corn meal agar plates or agar plates containing a desired fermentation media. Additionally, species of *Mortierella* sect. *schmuckeri* can be isolated from aquatic habitats using techniques known in the art (see, for example, U.S. Pat. No. 5,130,242, by Barclay et al., issued Jul. 14, 1992; and U.S. Pat. No. 5,340,594, by Barclay et al., issued Aug. 23, 1994). On agar plates, *Mortierella* colonies can be partly identified by several characteristics, including for example, as white colored colonies which grow essentially within the agar rather than predominantly exhibiting aerial growth. *Mortierella* colonies can also be distinguished from other fungi using the general characteristics of fungal taxonomy outlined, for example, by Talbot (Principles of Fungal Taxonomy, 1971, Macmillan Press). After isolation of a pure colony, members of the genus *Mortierella* can also be identified by, for example, a garlic-like odor when cultured in a shake flask or in agar plate cultures containing media described in Stevens, *ibid*. The culture producing the best sporulation can then be used to identify the species of the culture using the *Mortierella* keys outlined in Gams (pp. 381–391, 1977, *Persoonia*, Vol. 9; and in *Taxonomic problems in Mortierella*, Abstracts, 2nd International Mycological Conference, University of South Florida, Tampa, published by Hamilton Newell, Inc., Amherst, Mass.).

After isolation of a pure colony of strains of *Mortierella* sect. *schmuckeri*, the biomass of the strain can be analyzed for lipid content and arachidonic acid content by gas chromatography. Preferred colonies that exhibit rapid growth and high lipid and high arachidonic acid content can then be selected. Further selection for the presence or absence of other characteristics can also be conducted. For example, in the application of extracted lipids in infant formula for the benefit of arachidonic acid content, the presence of eicosapentanoic acid (C20:5n-3; "EPA") is detrimental. Therefore, one can select for the absence of high EPA content.

One preferred species of *Mortierella* sect. *schmuckeri* of the present invention is *Mortierella camargensis*. Particularly preferred strains of *Mortierella camargensis* of the present invention have the identifying characteristic of being able to produce about 0.86 grams of arachidonic acid per liter per day. Another identifying characteristic is that between about 25% and about 33% of the total fatty acids produced by such particularly preferred *Mortierella camargensis* can be arachidonic acid. Thus, the resulting arachidonic acid content of a biomass of a particularly preferred *Mortierella camargensis* of the present invention can be between about 9.6% and about 10.8% under appropriate fermentation conditions. Yet another identifying characteristic is that the resulting oil recovered from a particularly preferred *Mortierella camargensis* of the present invention can have an arachidonic acid content ranging from about 20% to about 30% of the total fatty acids.

Another particularly preferred species of *Mortierella* sect. *schmuckeri* of the present invention, *Mortierella schmuckeri* has the identifying characteristic of being able to produce about 0.84 grams of arachidonic acid per liter per day. Another identifying characteristic is that between about 40% and about 49% of the total fatty acids produced by such particularly preferred *Mortierella schmuckeri* of the present invention can be arachidonic acid. Thus, the resulting arachidonic acid content of a biomass of a particularly preferred *Mortierella schmuckeri* of the present invention can be between about 12.5% and about 13.6% under appropriate fermentation conditions. Yet another identifying characteristic is that the resulting oil recovered from a particularly preferred *Mortierella schmuckeri* can have an arachidonic acid content ranging from about 33% to about 41% of the total fatty acids.

It is within the scope of the present invention that, in addition to known strains of *Mortierella* sect. *schmuckeri*, such as those on deposit with the American Type Culture Collection (e.g., ATCC), newly identified strains from nature and mutant strains derived from known or newly identified strains, can be used to produce arachidonic acid. Naturally-occurring mutants of a parental strain of *Mortierella* sect. *schmuckeri* that are capable of producing arachidonic acid can be isolated by, for example, subjecting a parental strain to at least one round of chemical or physical mutagenesis in order to increase the rate of mutagenesis, thereby increasing the probability of obtaining a microorganism producing increased amounts of arachidonic acid. It will be obvious to one skilled in the art that mutant microorganisms of the present invention also include arachidonic acid-producing microorganisms that can be obtained by genetically-engineering microorganisms to produce increased amounts of arachidonic acid. For example, it is within the purview of the present invention to transform *Mortierella* sect. *schmuckeri* microorganisms with nucleic acid molecules encoding enzymes of the arachidonic acid biosynthetic pathway obtained from fungal arachidonic acid-producing microorganisms, such as those of the genus *Mortierella* sect. *schmuckeri*. A *Mortierella* sect. *schmuckeri* nucleic acid molecule of the present invention can be obtained from its natural source either as an entire (i.e., complete) gene or a portion thereof capable of forming a stable hybrid with the entire gene. A nucleic acid molecule from a strain of *Mortierella* sect. *schmuckeri* can also be produced using recombinant DNA technology (e.g., polymerase chain reaction (PCR) amplification, cloning) or chemical synthesis. As used herein, a "mutated microorganism" is a mutated parental microorganism in which the nucleotide composition of such microorganism has been modified by mutation(s) that occur naturally, that are the result of exposure to a mutagen, or that are the result of genetic engineering.

Preferred mutants of strains of *Mortierella* sect. *schmuckeri* of the present invention have one or more of the identifying characteristics of a preferred *Mortierella camargensis* of the present invention and a preferred *Mortierella schmuckeri* of the present invention as described in detail above.

In accordance with the present invention, microorganisms of the genus *Mortierella* sect. *schmuckeri* capable of producing arachidonic acid, are cultured in an effective medium, herein defined as any medium capable of promoting arachidonic acid production. Preferably, the effective medium also promotes rapid fungal growth. The microorganisms of the genus *Mortierella* sect. *schmuckeri* of the present invention can be cultured in conventional fermentation modes, which include, but are not limited to, batch, fed-batch, and continuous.

The present invention provides a method to produce arachidonic acid, comprising culturing microorganisms of the genus *Mortierella* sect. *schmuckeri* in a medium comprising a source of assimilable organic carbon and a source of assimilable nitrogen.

Sources of assimilable carbon include but are not limited to sugars and their polymers, including starches, dextrin, saccharose, maltose, lactose, glucose, fructose, mannose, sorbose, arabinose, xylose, levulose, cellobiose, and molasses; fatty acids; and polyalcohols such as glycerine. Preferred carbon sources in the present invention include monosaccharides, disaccharides, and trisaccharides. The most preferred carbon source is glucose.

Sources of assimilable nitrogen useful for fermentation of a microorganism of the present invention include simple nitrogen sources, organic nitrogen sources ad complex nitrogen sources. Such nitrogen sources include ammonium salts and substances of animal, vegetable and/or microbial origin. Such organic nitrogen sources include corn steep liquor, protein hydrolysates, microbial biomass hydrolysates, soy tone, soy meal, fish meal, meat meal, meat extract, peptone, tryptone, yeast extract, yeast, whey, ammonium sulfate, urea, ammonium nitrate and amino acids.

Preferred nitrogen sources for use in an effective medium of the present invention include complex nitrogen sources. Use of a complex nitrogen source in a fermentation medium of the present invention increases arachidonic acid production by a strain of *Mortierella* sect. *schmuckeri* of the present invention by at least about 50 percent and preferably by at least about 100 percent, either as measured by percent dry weight or percent total fatty acids in an oil, compared with a strain of *Mortierella* sect. *schmuckeri* grown in the absence of a complex nitrogen source. Suitable complex nitrogen sources include, for example, corn steep liquor, protein hydrolysates, microbial biomass hydrolysates, soy tone, soy meal, fish meal, meat meal, meat extract, peptone, tryptone, yeast extract, yeast and whey. One of skill in the art can determine which complex nitrogen source best stimulates arachidonic acid production in the strain of *Mortierella* sect. *schmuckeri* employed in a fermentation process.

In a preferred embodiment of the present invention, a fermentation is conducted in which a non-carbon nutrient, for example, nitrogen or magnesium and preferably nitrogen, is limited. In this manner, cellular metabolism is directed towards lipid production, thus enhancing the overall production of arachidonic acid.

The effective medium can contain other compounds such as inorganic salts, vitamins, trace metals or growth promoters. Such compounds can be present in carbon, nitrogen, or mineral sources in the effective medium or can be added specifically to the medium. Low concentrations of magnesium are also preferred.

During the fermentation, variables including the oxygen content, pH, temperature, carbon dioxide content, and rate of carbon source addition are controlled to maximize the production of arachidonic acid without unduly limiting the length of time during which successful fermentation can be accomplished. The optimum oxygen concentration for arachidonic acid production can be determined for any particular population of *Mortierella* sect. *schmuckeri* by variation of the oxygen content of the medium. In particular, the oxygen content of the fermentation medium is maintained at an oxygen content preferably ranges from between about 20% of saturation and about 60% of saturation.

Growth of strains of *Mortierella* sect. *schmuckeri* of the present invention can be effected at any temperature conducive to satisfactory growth of the strain; for example, between about 25° C. and about 33° C., preferably between about 27° C. and about 32° C., and more preferably at about 30° C. The culture medium typically becomes more alkaline during the fermentation if pH is not controlled by acid addition or buffers. The strains of *Mortierella* sect. *schmuckeri* of the present invention will grow over a pH range from between about 4.0 to about 10.0 with a starting pH of about 5.5 being more preferred.

Another aspect of the present invention includes a food product comprising a food material combined with microorganisms of the genus *Mortierella* sect. *schmuckeri*. Strains of *Mortierella* sect. *schmuckeri* of the present invention are added to a food material to create a food product having enhanced concentrations of arachidonic acid. As used herein, the term "food material" refers to any food type fed to humans or non-human animals. Also within the scope of the present invention is a method to make a food product comprising adding microorganisms of the genus *Mortierella* sect. *schmuckeri* to a food material.

*Mortierella* sect. *schmuckeri* of the present invention are recovered for use as a food supplement simply by separating the cells from fermentation medium. A variety of procedures can be employed in the recovery of microbial cells from the culture medium. In a preferred recovery process, the cells produced in the fermentation process are recovered from the culture medium by separation using conventional means, such as centrifugation or filtration. The cells can then be washed, frozen, lyophilized, and/or dried (e.g., spray drying, tunnel drying, vacuum drying, or a similar process). The arachidonic acid rich oil can be extracted immediately from the cells or the resulting cells can then be stored under a non-oxidizing atmosphere of a gas such as $N_2$ or $CO_2$ (to eliminate the presence of $O_2$) prior to incorporation into a food material. Alternatively, recovered cells can be used directly (without drying) as a feed supplement. To extend its shelf life, the wet biomass of a strain of *Mortierella* sect. *schmuckeri* can be acidified (approximate pH=3.5–4.5) and/or pasteurized or flash heated to inactivate enzymes and then canned, bottled or packaged under a vacuum.

A suitable food material useful for the formation of a food product of the present invention includes animal food. The term "animal" means any organism belonging to the kingdom Animalia and includes, without limitation, primates (e.g., humans and monkeys), livestock and domestic pets. The term "food product" includes any product to be fed to such animals. Preferred food materials to be consumed by humans includes infant formula and baby food. Preferred food materials to be consumed by domestic pets includes dog foods. By adding *Mortierella* sect. *schmuckeri* biomass or extracted oil to provide a source of arachidonic acid, preferred food products of the present invention comprise a total fatty acid content in which up to about 20% by weight of total fatty acids is arachidonic acid, more preferred food products of the present invention comprise a total fatty acid content in which up to about 10% by weight of total fatty acids is arachidonic acid, and even more preferred food products of the present invention comprise a total fatty acid content in which between about 0.1% and about 1.0% by weight of total fatty acids is arachidonic acid.

A further embodiment includes a food product comprising lipids recovered from a microorganism of the genus *Mortierella* sect. *schmuckeri* and a food material. Recovered lipids can include either all of the lipids recovered from the microorganisms or a portion thereof (i.e., isolated arachidonic acid or total fatty acids containing arachidonic acid). In the former instance, the lipid composition includes arachidonic acid in about the same relative amount as it exists in the organism. Alternatively, the recovered lipids can be further processed to concentrate the arachidonic acid to achieve a composition having a greater concentration of arachidonic acid than occurs naturally in the organism. Also within the scope of the present invention is a method to make a food product comprising adding lipids recovered from a microorganism of the genus *Mortierella* sect. *schmuckeri* to a food material.

Recovery of lipids from strains of *Mortierella* sect. *schmuckeri* can be accomplished by any suitable method, including numerous methods known in the art. For example, recovery can include the following method. Harvested cells (fresh or dried) can be ruptured using techniques known to those in the art. Lipids can then be extracted from the cells by any suitable means, such as by supercritical fluid extraction, or by extraction with solvents such as chloroform, hexane, methylene chloride, methanol, isopropol, ethyl acetate, and the like, and the extract evaporated under reduced pressure to produce a sample of concentrated lipid material. Arachidonic acid can be further separated from other lipids by chilling a fatty acid composition such that the saturated fatty acids in the composition precipitate out while the arachidonic acid remains in solution. The solution can then be recovered.

The *Mortierella* sect. *schmuckeri* microorganisms can also be broken or lysed and the lipids recovered into edible oil using standard methods known in the art. The recovered oils can be refined by well-known processes routinely employed to refine vegetable oils (e.g., chemical or physical refining). These refining processes remove impurities from recovered oils before they are used or sold as edible oils. The refining process consists of a series of processes to degum, bleach, filter, deodorize and polish the recovered oils. After refining, the oils can be used directly as a feed or food additive to produce arachidonic acid enriched products. Alternatively, the oil can be further processed and purified as outlined below and then used in the applications as described herein.

Lipids recovered from the biomass of a strain of *Mortierella* sect. *schmuckeri* of the present invention can be combined with any animal food material, particularly food materials for humans, to create a food product having enhanced concentrations of arachidonic acid. The amount of fatty acids naturally in food products varies from one food product to another. A food product of the present invention can have a normal amount of arachidonic acid or a modified amount of arachidonic acid. In the former instance, a portion of the naturally occurring lipids are substituted by lipids of the present invention. In the latter instance, naturally occurring lipids are supplemented by lipids of the present invention.

Preferably, lipids recovered from strain of *Mortierella* sect. *schmuckeri* are added to foods for infants, such as infant formula and baby food. According to the present invention, an infant refers to infants in utero and children less than about two years old, including, in particular, premature infants. Arachidonic acid is a particularly important component of infant formula and baby food because of the rapid growth of infants (i.e., doubling or tripling in weight during the first year of life). An effective amount of arachidonic acid to supplement infant formula is an amount that approximates the concentration of arachidonic acid in human breast milk. Preferred amounts of arachidonic acid to add to infant formula or baby food range from between about 0.1 to about 1.0% of total fatty acids, more preferably from between about 0.1 to about 0.6% of total fatty acids, and even more preferably about 0.4% of total fatty acids.

Arachidonic acid produced by the method of the present invention is suitable for use as therapeutic and experimental agents. An embodiment of the present invention comprises the production of arachidonic acid for treatment of arachidonic acid-deficient infants. The arachidonic acid can be included in a parenteral formulation that can be administered to an infant through parenteral routes to fortify the infant's supply of arachidonic acid. Preferred parenteral routes include, but are not limited to, subcutaneous, intradermal, intravenous, intramuscular and intraperitoneal routes. A parenteral formulation can include arachidonic acid of the present invention and a carrier suitable for parenteral delivery. As used, herein, a "carrier" refers to any substance suitable as a vehicle for delivering a molecule or composition to a suitable in vivo site of action. Examples of such carriers include, but are not limited to water, phosphate buffered saline, Ringer's solution, dextrose solution, serum-containing solutions, Hank's solution and other aqueous physiologically balanced solutions. Acceptable protocols to administer arachidonic acid in an effective manner include individual dose size, number of doses, frequency of dose administration, and mode of administration. Determination of such protocols can be accomplished by those skilled in the art depending upon a variety of variables, including the weight of the infant and the extent of arachidonic acid deficiency. Another embodiment of the present invention comprises the production of arachidonic acid for treatment of adults, in particular pregnant mothers. Acceptable protocols for administration of arachidonic acid to adults includes parenteral feeding techniques or encapsulating oil recovered from a microorganism of the present invention in a capsule, such as gelatin (i.e., digestible) capsule, for oral administration and/or in a liquid diet formulation. A liquid diet formulation can comprise a liquid composition containing nutrients suitable for supplementing a diet or nutrients sufficient as a complete diet.

Another embodiment of the present invention comprises the production of arachidonic acid for use as an experimental reagent to identify regulators of metabolic pathways for which arachidonic acid is a precursor. For example, arachidonic acid is a precursor for leukotrienes. Leukotrienes are believed to be involved in the occurrence of certain diseases involving inflammation and allergy. As such, inhibitors of leukotriene production may be valuable therapeutic agents. Arachidonic acid recovered using the method of the present invention can be used to test putative inhibitory agents in vitro by incubating the putative inhibitor with arachidonic acid under suitable conditions well-known to those of skill in the art, and measuring leukotriene production.

The following examples and test results are provided for the purposes of illustration and are not intended to limit the scope of the invention.

EXAMPLES

Example 1

This example describes the production of arachidonic acid by the strain S12 of *Mortierella* sect. *schmuckeri* which is a strain of *Mortierella schmuckeri*.

A strain of *Mortierella schmuckeri* was identified in accordance with the method of the present invention. Such strain is referred to herein as strain S12. A one centimeter squared portion of a *Mortierella schmuckeri* strain S12 was cut from a solid agar plate and placed in 100 ml aliquots of medium containing 10 grams/liter (g/l) of corn steep liquor, 0.1 g/l $CaCO_3$, 0.1 g/l $MgSO_4 \cdot 7H_2O$, 0.5 g/l $KH_2PO_4$, 1 milliliter per liter (ml/l) PII metals (6.0 g $Na_2EDTA$; 0.24 g $FeCl_3\text{-}6H_2O$; 6.84 g $H_3BO_3$; 0.86 g $MnCl_2\text{-}4H_2O$; 0.133 g $ZnSO_4\text{-}7H_2O$; 0.026 g $CoCl_2\text{-}6H_2O$; 0.005 g $NaMoO_4\text{-}2H_2O$; 0.002 g $CuSO_4\text{-}5H_2O$ and 0.052 g $NiSO_4\text{-}6H_2O$; dissolved in 1 liter of water and pH adjusted to 8.0), and 1 ml/l vitamin mix (100 mg/L thiamin; 500 µg/L biotin and 500 µg/L vitamin $B_{12}$), contained in 250 ml baffled shake flasks. The cultures were incubated for 72 hours, at 30° C. on a rotary shaker (225 rpm). After 72 hours, the cultures were of high density and had stopped growing.

The cells in the flasks were then sampled to determine ash-free dry weights and to quantify the fatty acid content of the cells. The cells of *Mortierella schmuckeri* strain S12 were harvested and centrifuged. Fatty acids in dry biomass of harvested cells were then methylated in 4% methanolic $H_2SO_4$ (4 ml $H_2SO_4$ in 96 ml methanol) at 100° C. for 1 hour. The fatty acid methyl esters were then quantified by gas chromatography (Varian 3500 gas chromatograph, Supelco SP 2330 column; initial column temp.=70° C.; detector temp=250° C.; injector temp=220° C.; carrier gas=helium; temperature program: initial column temp=70° C. for 3 min, 20° C. per min to 195° C., then hold for 5 min., then 25° C. per min to 220° C., then hold for 8 min.). The composition of the fatty acids in the fungal biomass is shown in Table 1.

TABLE 1

S12 Fatty Acid Profile

| FATTY ACID | | Fatty Acid Content | |
|---|---|---|---|
| | | mg/g dwt* | % TFA* |
| MYRISTATE | C14:0 | 0.9 | 0.3 |
| MYRISTOLEATE | C14:1 | 1.1 | 0.3 |
| PALMITATE | C16:0 | 45.6 | 13.5 |
| PALMITOLEATE | C16:1 | 2.2 | 0.6 |
| STEARATE | C18:0 | 26.9 | 8.0 |
| OLEATE | C18:1 | 39.8 | 11.8 |
| LINOLEATE | C18:2N6 | 36.5 | 10.8 |
| Gamma-LINOLENATE | C18:3N6 | 13.8 | 4.1 |
| LINOLENATE | C18:3N3 | 1.6 | 0.5 |
| EICOSENOATE-11 | C20:1 | 1.1 | 0.3 |
| EICOSADIENOATE-11,14 | C20:2 | 2.2 | 0.6 |
| HOMOGAMMA LINOLENATE | C20:3N6 | 1.6 | 0.5 |
| BEHENATE | C22:0 | 17.4 | 5.2 |

TABLE 1-continued

S12 Fatty Acid Profile

| | | Fatty Acid Content | |
|---|---|---|---|
| FATTY ACID | | mg/g dwt* | % TFA* |
| ARACHIDONATE | C20:4 | 135.7 | 40.3 |
| LIGNOCERATE | C24:0 | 9.6 | 2.8 |
| NERVONATE | C24:1 | 0.6 | 0.2 |
| | | 336.5 | 100.0 |

*TFA = Total Fatty Acids
*dwt = cellular dry weight

The results indicated that under these fermentation conditions, the strain S12 biomass contained about 33.7% of fatty acids. Approximately 40.3% of the total fatty acids was comprised of arachidonic acid. The arachidonic acid content of the biomass therefore was 13.6% cellular dry weight.

Example 2

This example describes the effect of varying the carbon to nitrogen ratio in the fermentation medium on arachidonic acid production in the fermentation of *Mortierella schmuckeri* strain S12 cells.

Fermentation cultures were prepared as described in Example 1. Numerous fermentation samples were prepared that had increasing concentrations of glucose (the amounts are shown in Table 2, first column). The relative amounts of total fatty acids and arachidonic acid were measured according to the method described in Example 1 and the results are illustrated in Table 2.

TABLE 2

Strain S12: Effect of C:N Ratio on Dry Weight, Lipid and Arachidonic Acid Yields

| glucose g/L | C:N Ratio | Biomass dry wt. g/L | Final pH | Tot. FA % dry wt. | Arachidonic % Tot. FA. | Arachidonic % dry wt. |
|---|---|---|---|---|---|---|
| 3.7 | 3:1 | 3.1 | 7.3 | 15.9 | 48.6 | 7.7 |
| 6.2 | 5:1 | 4.0 | 7.1 | 24.0 | 43.4 | 10.4 |
| 12.4 | 10:1 | 6.0 | 6.6 | 31.3 | 35.5 | 11.1 |
| 37.2 | 30:1 | 6.2 | 6.5 | 31.5 | 35.6 | 11.2 |
| 49.6 | 40:1 | 6.6 | 6.5 | 32.0 | 37.5 | 12.0 |
| 74.4 | 60:1 | 6.8 | 6.4 | 30.9 | 39.3 | 12.1 |
| 99.2 | 80:1 | 5.8 | 6.4 | 25.7 | 37.8 | 9.7 |
| 124.0 | 100:1 | 5.9 | 6.4 | 25.5 | 37.4 | 9.5 |

The results indicated that optimal carbon to nitrogen ratio for the fermentation of strain S12 is about 40:1 to about 60:1. The results also indicate that the amount of arachidonic acid produced by S12 cells can be increased by limiting the amount of non-carbon nutrients, in particular nitrogen, in the fermentation medium.

Example 3

This example illustrates the effect of nutrient manipulation on arachidonic acid production by *Mortierella schmuckeri* strain S12 and *Mortierella camargensis* strain S3.

A strain of *Mortierella camargensis* was identified in accordance with the method of the present invention. Such strain is referred to herein as strain S3. Fermentation cultures were prepared as described in Example 1. Numerous fermentation samples were prepared that had different nutrients deleted from the fermentation medium. The nutrients deleted from the various fermentation samples are shown in Table 3 (first column). The relative amounts of total fatty acids and arachidonic acid were measured according to the method described in Example 1. The results are shown in Table 3.

TABLE 3

Strains S12 and S3: Evaluation of nutrient subtraction on ARA production

| Nutrient Deleted | Biomass dwt yield g/L | Fatty acid % dwt | ARA % TFA | ARA % dwt | ARA g/L |
|---|---|---|---|---|---|
| Strain S12: *M. schmuckeri* | | | | | |
| CaCO$_3$ | 4.2 | 31.3 | 31.0 | 9.7 | 0.41 |
| Vitamins | 5.6 | 32.8 | 34.4 | 11.3 | 0.63 |
| MgSO$_4$ | 5.4 | 32.1 | 39.3 | 12.6 | 0.68 |
| PII | 5.5 | 30.6 | 34.3 | 10.5 | 0.58 |
| KH$_2$PO$_4$ | 5.5 | 30.3 | 35.3 | 10.7 | 0.59 |
| Strain S3: *M. camargensis* | | | | | |
| CaCO$_3$ | 4.5 | 37.4 | 21.9 | 8.2 | 0.37 |
| Vitamins | 5.5 | 34.9 | 24.9 | 8.7 | 0.48 |
| MgSO$_4$ | 5.4 | 38.7 | 25.3 | 9.8 | 0.53 |
| PII | 5.5 | 34.9 | 23.2 | 8.1 | 0.45 |
| KH$_2$PO$_4$ | 5.3 | 34.1 | 23.2 | 7.9 | 0.42 |

The results indicated that, for both strains of *Mortierella* sect. *schmuckeri*, minimizing the magnesium concentration in the fermentation medium had a greater effect on arachidonic acid production than deletion of calcium, vitamins, trace metals and potassium phosphate. For example, the amount of arachidonic acid produced by cells of strain S12 grown in the absence of magnesium was about 0.7 grams of arachidonic acid per liter, while the arachidonic acid production by cells of strain S12 grown in the absence of calcium was on average about 0.4 grams of arachidonic acid per liter.

Example 4

This example describes a comparison of arachidonic acid production by *Mortierella camargensis* strain S3 between cells grown in the presence or absence of corn steep liquor, a complex nitrogen source.

A first fermentation sample was prepared using the method and culture medium described in Example 1. A second fermentation sample was prepared using the medium described in Example 1 but instead of corn steep liquor, yeast extract was used as the nitrogen source. Lipids were prepared from strain S3 cells and analyzed using the method described in Example 1. The composition of the fatty acid mixture obtained from each of the foregoing fermentation procedures is shown in Tables 4 and 5. The S3 sample grown with corn steep liquor was found to contain 35.9% of dry weight as fatty acids. The arachidonic acid content of this sample was 10.8% of cellular dry weight. The S3 sample grown without corn steep liquor was found to contain 19.8% of dry weight as of fatty acids. The arachidonic acid content of the sample was 4.8% of cellular dry weight.

TABLE 4

S3 Strain Grown With Corn Steep Liquor

| FATTY ACID | | Fatty Acid Content | |
|---|---|---|---|
| | | mg/g dwt* | % TFA* |
| MYRISTATE | C14:0 | 1.8 | 0.5 |
| MYRISTOLEATE | C14:1 | 0.9 | 0.3 |
| PALMITATE | C16:0 | 60.1 | 16.7 |
| PALMITOLEATE | C16:1 | 1.0 | 0.3 |
| STEARATE | C18:0 | 30.3 | 8.4 |
| OLEATE | C18:1 | 27.9 | 7.8 |
| LINOLEATE | C18:2N6 | 51.4 | 14.3 |
| GAMMA-LINOLENATE | C18:3N6 | 27.5 | 7.7 |
| EICOSENOATE-11 | C20:1 | 1.5 | 0.4 |
| EICOSADIENOATE-11,14 | C20:2 | 3.1 | 0.9 |
| HOMOGAMMA LINOLENATE | C20:3N6 | 1.8 | 0.5 |
| BEHENATE | C22:0 | 28.2 | 7.8 |
| EICOSATRIENOATE | C20:3 | 0.6 | 0.2 |
| ARACHIDONATE | C20:4 | 107.8 | 30.0 |
| EICOSAPENTANOATE | C20:5N3 | 0.4 | 0.1 |
| LIGNOCERATE | C24:0 | 13.6 | 3.8 |
| NERVONATE | C24:1 | 0.8 | 0.2 |
| DOCOSAHEXANOATE | C22:6N3 | 0.6 | 0.2 |
| | | 359.4 | 100.0 |

*TFA = Total Fatty Acids
*dwt = cellular dry weight

TABLE 5

S3 Strain Grown Without Corn Steep Liquor

| FATTY ACID | | Fatty Acid Content | |
|---|---|---|---|
| | | mg/g dwt* | % TFA* |
| MYRISTATE | C14:0 | 1.0 | 0.5 |
| MYRISTOLEATE | C14:1 | 1.2 | 0.6 |
| PALMITATE | C16:0 | 38.9 | 19.7 |
| PALMITOLEATE | C16:1 | 0.8 | 0.4 |
| STEARATE | C18:0 | 9.7 | 4.9 |
| OLEATE | C18:1 | 33.6 | 17.0 |
| LINOLEATE | C18:2N6 | 28.1 | 14.2 |
| GAMMA-LINOLENATE | C18:3N6 | 11.8 | 6.0 |
| EICOSENOATE-11 | C20:1 | 1.9 | 0.9 |
| EICOSADIENOATE-11,14 | C20:2 | 1.0 | 0.5 |
| HOMOGAMMA LINOLENATE | C20:3N6 | 4.4 | 2.2 |
| BEHENATE | C22:0 | 7.0 | 3.6 |
| ARACHIDONATE | C20:4 | 48.8 | 24.7 |
| ERUCATE | C22:1 | 0.0 | 0.0 |
| EICOSAPENTANOATE | C20:5N3 | 0.0 | 0.0 |
| LIGNOCERATE | C24:0 | 8.7 | 4.4 |
| NERVONATE | C24:1 | 0.4 | 0.2 |
| DOCOSAHEXANOATE | C22:6N3 | 0.4 | 0.2 |
| | | 197.7 | 100.0 |

*TFA = Total Fatty Acids
*dwt = cellular dry weight

The results indicated that inclusion of corn steep liquor as a nitrogen source in the fermentation medium enhanced arachidonic acid production by S3 cells about two-fold. For example, S3 cells grown in the presence of corn steep liquor produced about 107.8 milligrams of arachidonic acid per gram of fungal biomass. Arachidonic acid comprised about 30% of the total fatty acids. Conversely, S3 cells grown in the absence of corn steep liquor produced about 48.8 milligrams of arachidonic acid per gram of fungal biomass. Arachidonic acid comprised about 24.7% of the total fatty acids. Thus, fermentation in the presence of corn steep liquor (a complex nitrogen source) enhanced the production of arachidonic acid.

The results indicate that corn steep liquor is one of the best complex nitrogen sources for stimulating arachidonic acid production in Strain S3. Arachidonic acid production, however, by Strain S12 (*Mortierella schmuckeri*) is stimulated by a wider range of complex nitrogen including, but not limited to, corn steep liquor, yeast extract, yeast, whey and soy flour.

Example 5

This example describes a comparison between the arachidonic acid content of *Mortierella camargensis* strain S3 and *Mortierella schmuckeri* strain S12 with previously known ATCC strains of the *schmuckeri* section of *Mortierella*.

Four strains, *Mortierella camargensis* strain S3, *Mortierella schmuckeri* strain S12 and *Mortierella schmuckeri* (ATCC No. 42658) were cultured in the presence or absence of corn steep liquor as described in Example 4. The fatty acid content of the cells of the S3 strain and the two known strains was measured according to the method described in Example 1. A comparison of the total fatty acid yield and arachidonic acid yields is shown below in Table 6.

TABLE 6

Comparison of Arachidonic Acid and Total Fatty Acid Production in Strains of Mortierella from the Schmuckeri Group of this Fungus

| | w/o csl | w/ csl |
|---|---|---|
| Total Fatty Acids (as % dwt) | | |
| *Mortierella camargensis* (Strain S3) | 19.8 | 35.9 |
| *Mortierella schmuckeri* (Strain S12) | 18.3 | 33.7 |
| *Mortierella schmuckeri* (ATCC 42658) | 28.2 | 38.0 |
| Arachidonic Acid (as % dwt) | | |
| *Mortierella camargensis* (Strain S3) | 4.9 | 10.7 |
| *Mortierella schmuckeri* (Strain S12) | 6.0 | 13.6 |
| *Mortierella schmuckeri* (ATCC 42658) | 2.5 | 2.4 |
| Arachidonic Acid (as % total fatty acids) | | |
| *Mortierella camargensis* (Strain S3) | 24.7 | 30.0 |
| *Mortierella schmuckeri* (Strain S12) | 32.6 | 40.3 |
| *Mortierella schmuckeri* (ATCC 42658) | 9.0 | 6.3 | w/o csl = without corn steep liquor
w/ csl = with corn steep liquor
% dwt = percent dry weight of biomass From the results shown in Table 6 it can be seen that the presence of corn steep liquor in the fermentation medium increases the total fatty acid production by about 2-fold in strain S3 and S12, and by about one third in *Mortierella schmuckeri* (ATCC No. 42658). However, while the presence of corn steep liquor in the fermentation medium increased arachidonic acid content (as % dwt) by about 2-fold in strain S3, the corn steep liquor did not effect arachidonic acid production by *Mortierella schmuckeri* (ATCC No. 42658). *Mortierella clausenii* (ATCC No. 64864) showed no significant growth in either the presence or absence of corn steep liquor.

Example 6

This example describes the analysis of the fermentation productivity and lipid content of oil obtained from the *Mortierella schmuckeri* strain S12.

Fermentations were conducted using *Mortierella schmuckeri* strain S12 in two 14 liter fermentation cultures designated vessel B20 and B23. M-3 medium was utilized in vessel B20 and M-6 medium was utilized in vessel B23. M-3 medium contained 12 g/L Cargill 200/20 soy flour, 0.1 g/L MgSO$_4$-7H$_2$O, 0.1 g/L CaCO$_3$, 1 ml/L of PII Metals, 1 ml/l of Vitamin mix, 2 g/L of KH$_2$PO$_4$, 43.8 g/L of glucose and 0.5 ml/L of K60K antifoam. M-6 medium has the same ingredients as the M-3 medium except that it contained 12 g/L of Nutrex 55 (Red Star Specialty Products, Milwaukee, Wis.), a spray dried form of inactive Bakers yeast, instead of soy flour. The oil samples were purified and analyzed for arachidonic acid (ARA) content. The results of these two fermentations are shown in Table 7 below.

TABLE 7

ARA Production by S12 cells from Large Fermentations

| Vessel | Approx. Biomass Yield | Approx. ARA Yield | Ferm. Time | ARA Prod. |
|---|---|---|---|---|
| B23 | 22 g/L | 2.3 g/L | 65.5 h | 0.84 g/L/day |
| B20 | 20 g/L | 2.3 g/L | 65.5 h | 0.84 g/L/day |

Oil was extracted from the fungal biomass produced in the two fermentations according to the following process. Samples of S12 fermentation broth from vessels B23 and B20 were filtered under vacuum to produce a cake of biomaterial which was isolated and dried in a steam oven. The dried biomaterial (200 g) was extracted with hexane (2×600 ml) in a waring blender to simulate a wet milling process. The milled fungal biomass was filtered to remove solids and the hexane was evaporated to afford a crude oil. Approximately 75% of the theoretical oil content was recovered in this wet milling process. The crude oil was purified by passing through a column of silica gel and the neutral oil fraction (triacylglycerides) was isolated by eluting the column with 30% ethanol:acetic acid in hexane. Fractions containing neutral oil (90% of crude oil) were pooled and concentrated to give a pure oil fraction which was analyzed by gas liquid chromatography. The results of the fatty acid analyses performed on the purified oil samples are shown in Table 8 below.

TABLE 8

Fatty Acid Content of S12 Oil

| Fatty Acid | % FATTY ACID | |
|---|---|---|
| | S-12 (B20) | S-12 (B23) |
| C16:0 Palmitate | 10 | 11 |
| C18:0 Stearate | 12 | 12 |
| C18:1 n-9 Oleate | 14 | 16 |
| C18:2 n-6 Linoleate | 10 | 9 |
| C18:3 n-6 GLA | 3 | 3 |
| C20:0 Arachidate | 1 | 1 |
| C20:3 n-6 Homo GLA | 3 | 3 |
| C20:4 n-6 Arachidonic Acid | 41 | 37 |
| C22:0 Behenate | 2 | 2 |
| C24:0 Lignocerate | 4 | 4 |

The results indicate that the purified oil obtained from biomass produced in vessel B20 contained 41% arachidonic acid and the oil from the biomass produced in vessel B23 contained 37% arachidonic acid.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. A food product comprising:
   (a) a microorganism of the genus *Mortierella* sect. *schmuckeri*, lipids recovered from said microorganism or mixtures thereof; and
   (b) a food material,
   wherein at least about 21.9% of the total fatty acid of a biomass of said *Mortierella* sect. *Schmuckeri* is arachidonic acid, and wherein said *Mortierella* sect. *schmuckeri* is capable of producing at least about 0.7 grams of arachidonic acid per liter per day.

2. The food product of claim 1, wherein said food material comprises animal food.

3. The food product of claim 1, wherein said food material comprises human food.

4. The food product of claim 1, wherein said *Mortierella* sect. *schmuckeri* is of the species *Mortierella schmuckeri*.

5. The food product of claim 1, wherein said *Mortierella* sect. *schmuckeri* is of the species *Mortierella camargensis*.

6. The food product of claim 1, wherein said food product has a total fatty acid content in which up to about 20% by weight of total fatty acids is arachidonic acid.

7. The food product of claim 1, wherein said food product has a total fatty acid content in which up to about 10% by weight of total fatty acids is arachidonic acid.

8. The food product of claim 1, wherein said food product has a total fatty acid content in which between about 0.1% and about 1.0% by weight of total fatty acids is arachidonic acid.

9. The food product of claim 1, wherein said food material comprises an infant food material.

10. The food product of claim 1, wherein said food product is selected from the group consisting of infant formula and baby food.

* * * * *